(12) United States Patent
Jalal et al.

(10) Patent No.: US 12,341,776 B2
(45) Date of Patent: Jun. 24, 2025

(54) SERVICE TO SERVICE COMMUNICATION AND AUTHENTICATION VIA A CENTRAL NETWORK MESH

(71) Applicant: Genentech, Inc., South San Francisco, CA (US)

(72) Inventors: Niaz Ahsan Jalal, South San Francisco, CA (US); Abdesslem Dridi, South San Francisco, CA (US)

(73) Assignee: GENENTECH, INC., South San Francisco, CA (US)

( * ) Notice: Subject to any disclaimer, the term of this patent is extended or adjusted under 35 U.S.C. 154(b) by 225 days.

(21) Appl. No.: 18/312,561

(22) Filed: May 4, 2023

(65) Prior Publication Data
US 2024/0129306 A1 Apr. 18, 2024

Related U.S. Application Data (63) Continuation of application No. PCT/US2021/058402, filed on Nov. 8, 2021.

(60) Provisional application No. 63/111,997, filed on Nov. 10, 2020.

(51) Int. Cl.
*H04L 9/40* (2022.01)

(52) U.S. Cl.
CPC .......... *H04L 63/0876* (2013.01); *H04L 63/10* (2013.01); *H04L 63/20* (2013.01)

(58) Field of Classification Search
CPC ...... H04L 63/0876; H04L 63/10; H04L 63/20
USPC .......................................................... 726/4
See application file for complete search history.

(56) References Cited

U.S. PATENT DOCUMENTS

| | | | |
|---|---|---|---|
| 11,153,184 B2* | 10/2021 | Yadav | H04L 63/1416 |
| 12,155,731 B2 | 11/2024 | Joshi et al. | |
| 2006/0026042 A1* | 2/2006 | Awaraji | G06F 21/6245 |
| | | | 707/999.009 |
| 2007/0106754 A1* | 5/2007 | Moore | G16H 40/20 |
| | | | 707/E17.116 |

(Continued)

FOREIGN PATENT DOCUMENTS

WO 2019169405 A1 9/2019

OTHER PUBLICATIONS

International Application No. PCT/US2021/058418, "International Search Report and Written Opinion", Feb. 11, 2022, 14 pages.

(Continued)

*Primary Examiner* — David P Zarka
(74) *Attorney, Agent, or Firm* — Kilpatrick Townsend & Stockton LLP (57) ABSTRACT

The present disclosure relates to techniques for service to service communication and authentication via a network mesh. Particularly, aspects are directed to receiving, at a network mesh, a service request for a first service, and obtaining information associated with the first service. The information includes a location of a first pod encapsulating the first service. The network mesh using the location of the first pod, retrieves security rules specific for the first pod. The network mesh forwards the service request to the first service based on the security rules of the first pod and obtains results of the service request from the first service. The results include a sub result obtained from a second service in accordance with security rules for the first pod encapsulating the first service and security rules for a second pod encapsulating the second service.

20 Claims, 4 Drawing Sheets

(56) References Cited

U.S. PATENT DOCUMENTS

| | | | |
|---|---|---|---|
| 2017/0103231 A1* | 4/2017 | Lipman | G06F 21/6245 |
| 2018/0359239 A1* | 12/2018 | Schwarz | H04L 63/083 |
| 2019/0098037 A1* | 3/2019 | Shenoy, Jr. | H04L 63/1441 |
| 2019/0156023 A1 | 5/2019 | Gerebe et al. | |
| 2020/0162380 A1 | 5/2020 | Pilkington et al. | |
| 2020/0195495 A1* | 6/2020 | Parker | H04L 41/40 |
| 2020/0241867 A1 | 7/2020 | Gainsborough et al. | |
| 2020/0280592 A1 | 9/2020 | Ithal et al. | |
| 2020/0412651 A1* | 12/2020 | Patidar | H04L 63/0471 |
| 2021/0311764 A1 | 10/2021 | Rosoff et al. | |
| 2022/0038544 A1* | 2/2022 | Grinstein | H04L 63/0853 |
| 2022/0244993 A1 | 8/2022 | Macdonald et al. | |

OTHER PUBLICATIONS

Ravula, "Achieving Continuous Delivery of Immutable Containerized Microservices with Mesos/Marathon", Aalto University, Thesis for the degree of Master of Science in Technology, May 19, 2017, pp. 1-84.

Li et al., "Service Mesh: Challenges, State of the Art, and Future Research Opportunities", IEEE International Conference on Service-Oriented System Engineering (SOSE), IEEE, Apr. 4, 2019, pp. 122-1225.

Dab et al., "An Efficient Traffic Steering for Cloud-Native Service Function Chaining", 23rd Conference on Innovation in Clouds, Internet and Networks and Workshops (ICIN), IEEE, 10.1109/ICIN48450.2020.9059340, Feb. 24, 2020, pp. 71-78.

International Application No. PCT/US2021/058402, "International Preliminary Report on Patentability", May 25, 2023, 9 pages.

International Application No. PCT/US2021/058402, "International Search Report and Written Opinion", Mar. 2, 2022, 12 pages.

International Application No. PCT/US2021/058418, "International Preliminary Report on Patentability", May 25, 2023, 12 pages.

* cited by examiner

SERVICE TO SERVICE COMMUNICATION AND AUTHENTICATION VIA A CENTRAL NETWORK MESH

PRIORITY CLAIM

This application is a continuation of International Application No. PCT/US2021/058402, filed on Nov. 8, 2021, which claims the benefit of and priority to U.S. Provisional Application No. 63/111,997, filed on Nov. 10, 2020, which is hereby incorporated by reference in its entirety for all purposes.

FIELD

The present disclosure relates to digital and personalized healthcare, and in particular to techniques for service to service communication and authentication via a centralized network mesh in a distributed computing environment.

BACKGROUND

In healthcare, data-driven technology solutions are being developed to further personalized healthcare all while reducing costs. With the healthcare landscape shifting to an on-demand deployment system of personalized medical services and solutions, healthcare providers are looking to developers for help with innovating solutions faster through automating and streamlining the software deployment and service management processes. In order to support healthcare providers and services, developers have looked to distributed computing environments (e.g., cloud computing) as the healthcare information technology infrastructure standard. Cloud computing has many benefits such as flexibility, cost and energy savings, resource sharing, and fast deployment. For example, cloud computing is capable of providing a complex infrastructure required to support software deployment and service management processes within various service models (e.g., analytics-as-a-service (AaaS)), which can help facilitate communication, collaboration, and coordination among different healthcare providers. Cloud computing can also help the healthcare industry deliver more value for the dollar. For example, cloud computing can offer fast, flexible, scalable, and cost-effective infrastructure and applications. The cloud computing can also help store, manage, protect, share, and archive electronic health records (EHRs), laboratory information system, pharmaceutical information system, and medical images.

While distributed computing environments such as cloud computing afford healthcare providers many benefits, they function differently than legacy storage or information sharing solutions, and thus create their own unique privacy and security challenges. The centralization of data on the cloud raises many security and privacy concerns for individuals and healthcare providers. This centralization of data provides attackers with one-stop shopping to steal data and intercept data in-motion and moves data ownership to the cloud service providers; therefore, the individuals and healthcare providers lose some control over sensitive data. As a result, security, privacy, efficiency, and scalability concerns are hindering the wide adoption of the cloud technology. For example, because users access data through an internet connection, government regulation (e.g., Health Insurance Portability and Accountability Act (HIPAA), "good practice" quality guidelines and regulations (GxP), and General Data Protection Regulation (GDPR) compliance becomes a unique challenge for healthcare providers looking into cloud solutions to support software deployment and service management processes. Accordingly, there is a need for advances in compliant software deployment platforms, built to ensure the confidentiality, availability and integrity of protected healthcare information.

SUMMARY

In some embodiments, a computer-implemented method is provided that comprises receiving, at a network mesh, a service request for a first service; obtaining, by the network mesh, information associated with the first service from a cache or service registry, wherein the information includes identification of a first pod comprising the first service and a location of the first pod within a first distributed computing environment; retrieving, by the network mesh using the location of the first pod, security rules for the first pod, wherein the security rules define: (i) a unique address identifier for the first service, and (ii) services that the first service is authorized to communicate with and access; forwarding, by the network mesh using the unique address identifier for the first service, the service request to the first service; receiving, by the network mesh, an access request from the first service to communicate with and access a second service, wherein the access request includes a security key specific to the second service; obtaining, by the network mesh, information associated with the second service from the cache or the service registry, wherein the information includes identification of a second pod comprising the second service and a location of the second pod within the first distributed computing environment or a second distributed computing environment; and retrieving, by the network mesh using the location of the second pod, security rules for the second pod, wherein the security rules define (i) a unique address identifier for the second service, and (ii) services that the second service is authorized to communicate with and access; forwarding, by the network mesh using the unique address identifier for the second service, the access request from the first service to the second service based on the security rules for the first pod and the security rules for the second pod; receiving, by the network mesh, a final result of the service request from the first service, wherein the final result includes a sub result obtained from the second service; and outputting, by the network mesh, the final result of the service request.

In some embodiments, the obtaining the information associated with the first service or the second service comprises: determining whether the information associated with the first service or the second service is available from the cache; when the information associated with the first service or the second service is available from the cache, obtaining the information associated with the first service or the second service from the cache; when the information associated with the first service or the second service is not available from the cache, obtaining the information associated with the first service or the second service from the registry; and in response to obtaining the information associated with the first service or the second service from the registry, storing the information associated with the first service or the second service in the cache for subsequent requests.

In some embodiments, the security key is obtained by the first service from a vault, and the first service embeds the security key into the access request.

In some embodiments, the access request from the first service further includes a request of the second service to perform one or more operations and/or acquire services on behalf of the first service.

In some embodiments, the second service performs the one or more operations and/or acquires the services on behalf of the first service; and generates the sub result based on the performance of the one or more operations and/or acquisition of the services.

In some embodiments, the second service validates the security key prior to performing the one or more operations and/or acquiring the services on behalf of the first service.

In some embodiments, the second pod is located within the second distributed computing environment, which is different from the first distributed computing environment.

In some embodiments, the security rules for the first pod further define: (i) a number of instances available for the first service, and (ii) which instances are available for processing the service request, and wherein the forwarding the service request to the first service comprises: determining the instances that are available for processing the service request based on the security rules for the first pod; and forwarding the service request to at least one of the instances of the first service.

In some embodiments, the forwarding the access request from the first service to the second service comprises: determining whether the security rules for the first pod define the second service as a service that the first service is authorized to communicate with and access; determining whether the security rules for the second pod define the first service as a service that the second service is authorized to receive communication from and allow to access; and when the second service is a service that the first service is authorized to communicate with and access and the first service is a service that the second service is authorized to receive communication from and allow to access, forwarding the access request from the first service to the second service.

In some embodiments, the security rules for the second pod further define: (i) a number of instances available for the second service, and (ii) which instances are available for processing the access request, and wherein the forwarding the access request from the first service to the second service further comprises: determining the instances that are available for processing the access request based on the security rules for the second pod; and forwarding the access request to at least one of the instances of the second service.

In some embodiments, the first service comprises one or more programs deployed onto one or more clusters packaged as a first container or first set of containers on the first distributed computing environment, and the first container or the first set of containers are packaged as the first pod, which is a higher-level structure that represents the one or more programs running on the one or more clusters; and the second service comprises one or more programs deployed onto one or more clusters packaged as a second container or second set of containers on the first distributed computing environment or a second distributed computing environment, and the second container or the second set of containers are packaged as the second pod, which is a higher-level structure that represents the one or more programs running on the one or more clusters.

Some embodiments of the present disclosure include a system including one or more data processors. In some embodiments, the system includes a non-transitory computer readable storage medium containing instructions which, when executed on the one or more data processors, cause the one or more data processors to perform part or all of one or more methods and/or part or all of one or more processes disclosed herein. Some embodiments of the present disclosure include a computer-program product tangibly embodied in a non-transitory machine-readable storage medium, including instructions configured to cause one or more data processors to perform part or all of one or more methods and/or part or all of one or more processes disclosed herein.

The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention as claimed has been specifically disclosed by embodiments and optional features, modification and variation of the concepts herein disclosed may be resorted to by those skilled in the art, and that such modifications and variations are considered to be within the scope of this invention as defined by the appended claims.

BRIEF DESCRIPTION OF THE DRAWINGS

The present disclosure is described in conjunction with the appended figures.

In the appended figures, similar components and/or features can have the same reference label. Further, various components of the same type can be distinguished by following the reference label by a dash and a second label that distinguishes among the similar components. If only the first reference label is used in the specification, the description is applicable to any one of the similar components having the same first reference label irrespective of the second reference label.

DETAILED DESCRIPTION

I. Overview

The present disclosure describes techniques for service to service communication and authentication via a centralized network mesh in a distributed computing environment. More specifically, embodiments of the present disclosure provide a network mesh that provides pod-level networking to make it possible for services to communicate with each other across multiple types of distributed computing environments in a secure manner. The network mesh and pod-level networking maintain isolation between services and resources such that it is easier to maintain control over where data is stored, who can access what data, what resources a service or user is able to consume at a given time, and ensure the right services and resources have the right access at all times, wherever the services or resources are running or stored.

Cloud computing offers opportunities and challenges. As with many other information technology solutions, the cloud has various security issues and concerns. Since cloud computing usually operates in an open and shared environment, it is often vulnerable for data loss, theft, and malicious attacks. Weak cloud security is one of the important problems that are hindering the full diffusion of the cloud computing in the healthcare industry. Healthcare professionals have many reasons not to trust cloud computing, for example, they cannot give away control over their medical records. Organizations and cloud providers usually store their data in different data centers located in different geographic locations. This represents a unique advantage, since data storage on the cloud will be redundant, and in case of force majeure, different data centers will help recover from disasters. On the other hand, this same advantage can pose a security challenge because data stored in different locations will be more prone to theft and loss. Additionally, data stored in different locations and the security thereof will be governed by various international, regional, and local regulations. In general, there are many security risks associated with the use of cloud computing, for example, failure to separate virtual users, identity theft, privilege abuse, and poor encryption are among some of these security risks.

To address these limitations and problems, the techniques for service to service communication and authentication in the present disclosure utilize pod-level networking governed by communication rules and security keys. In a digital and personalized healthcare environment there are typically multiple partners interacting with one another and these interactions need to be controlled in a secure manner to maintain isolation and traceability between services and resources. The services are any service (e.g., a healthcare related service such as data analytics or software as a medical device) that can be provided by one or more partners. The resources are in general hardware and software resources that support the services (e.g., memory and processing units); however, it should be understood that in certain instances the resource may also include data, algorithms, models, or the like (e.g., health care related data stored in a data store). In order to control these interactions in a secure manner, pod level security rules are provided that define which services are allowed to communicate with one another and which resources those services are allowed to access. Additionally, security keys (e.g., public/private key pair) are provided that allow the services to gain access to other services or resources. This two layered approach is facilitated by a centralized network mesh, which has access to the pod level security rules and locations of each service on one or more distributed computing environments, in order to maintain isolation and traceability between services and resources. For example, when a call for a service is received by the network mesh, the network mesh routes the call to the appropriate service based on the pod level security rules and information concerning the location of the service, and the service is able to gain access to other services and resources using the one or more security keys and proxy calls via the network mesh to perform various operations for providing the services.

One illustrative embodiment of the present disclosure is directed to a method that includes receiving, at a network mesh, a service request for a first service from a user; and obtaining, by the network mesh, information associated with the first service from a cache or service registry. The information includes identification of a first pod comprising the first service and a location of the first pod within a first distributed computing environment. The method further includes retrieving, by the network mesh using the location of the first pod, security rules for the first pod. The security rules define: (i) a unique address identifier for the first service, and (ii) services that the first service is authorized to communicate with and access. The method further includes forwarding, by the network mesh using the unique address identifier for the first service, the service request to the first service; and receiving, by the network mesh, an access request from the first service to communicate with and access a second service. The access request includes a security key specific to the second service. The method further includes obtaining, by the network mesh, information associated with the second service from the cache or the service registry. The information includes identification of a second pod comprising the second service and a location of the second pod within the first distributed computing environment or a second distributed computing environment. The method further includes retrieving, by the network mesh using the location of the second pod, security rules for the second pod. The security rules define (i) a unique address identifier for the second service, and (ii) services that the second service is authorized to communicate with and access. The method further includes forwarding, by the network mesh using the unique address identifier for the second service, the access request from the first service to the second service based on the security rules for the first pod and the security rules for the second pod; and receiving, by the network mesh, a final result of the service request from the first service. The final result includes a sub result obtained from the second service. The method further includes forwarding, by the network mesh, the final result of the service request to the user.

II. Digital Health Platform

Figure 1:
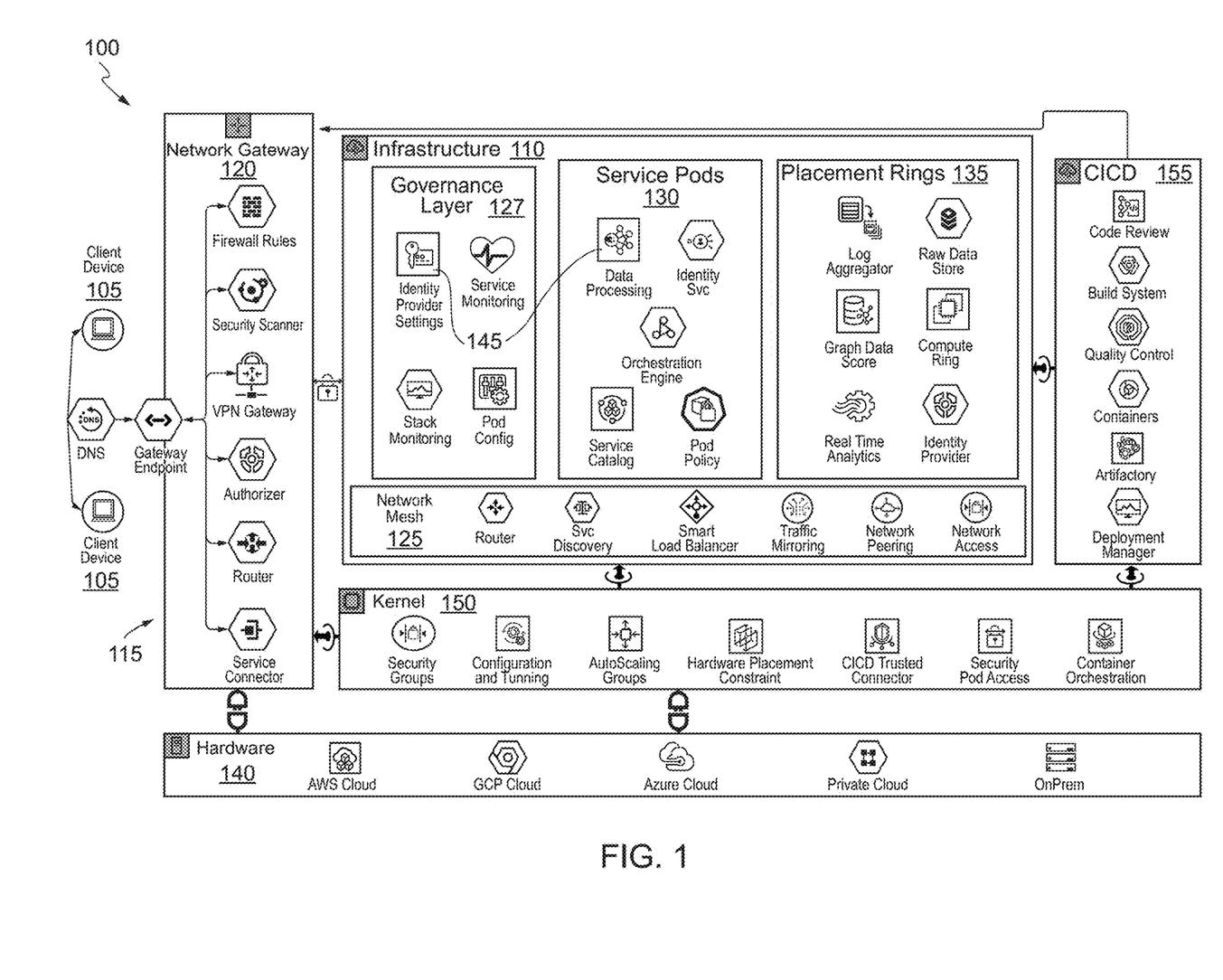
FIG. 1 depicts a diagram of a digital health platform for providing data-driven technology solutions according to various embodiments.

FIG. 1 depicts a simplified diagram of a digital health platform 100 for providing data-driven technology solutions in accordance with various embodiments. In the illustrated embodiment, digital health platform 100 includes client computing devices 105 coupled to a cloud based infrastructure 110 via a network(s) 115 including network gateway 120 and network mesh 125. The infrastructure 110 is adapted to execute services or software applications within service pods 130 using resources provisioned within placement rings 135 by cloud service providers 140 (e.g., a distributed computing environment) using various hardware and cloud infrastructure (e.g., private cloud or on-premise cloud infrastructure and public cloud infrastructure). These services or software applications may be offered as web-based or cloud services, such as under an AaaS or SaaS model to users of client computing devices 105. Several providers offer cloud services such as Amazon, Google, and Oracle. The term cloud service is generally used to refer to a service that is made available to users on demand and via a communication network such as the Internet by systems (e.g., infrastructure 110) of a service provider such as a healthcare provider or government regulated entity. Consumers may thus avail themselves of cloud services provided by a service provider without having to purchase separate licenses, support, or hardware and software resources that support the services. For example, a cloud service provider's system may host the one or more programs, and a user may, via the Internet, on demand, use the one or more programs without the user having to buy infrastructure resources for executing the one or more programs. Cloud services are designed to provide easy, scalable access to applications, resources and services.

In some instances, users (e.g., software or service consumers) operating client computing devices 105 utilize one or more client applications to consume the software products, services, or systems provided by various components 145 of the infrastructure 110. In other instances, users (e.g., developers) operating client computing devices 105 utilize one or more client applications to upload source code for the software products, services, or systems to be provided by the various components 145 of the infrastructure 110. The components 145 include software components that may be executed by one or more processors, hardware components, or combinations thereof. It should be appreciated that various different system configurations are possible, which may be different from those illustrated for the digital health platform 100. The embodiment shown in FIG. 1 is thus one example of a distributed computing environment for implementing a digital health platform and is not intended to be limiting.

The client computing devices 105 include various types of computing systems such as portable handheld devices, general purpose computers such as personal computers and laptops, workstation computers, wearable devices, gaming systems, thin clients, various messaging devices, sensors or other sensing devices, and the like. These computing devices may run various types and versions of software applications and operating systems (e.g., Microsoft Windows®, Apple Macintosh®, UNIX® or UNIX-like operating systems, Linux or Linux-like operating systems such as Google Chrome™ OS) including various mobile operating systems (e.g., Microsoft Windows Mobile®, iOS®, Windows Phone®, Android™ BlackBerry®, Palm OS®). Portable handheld devices may include cellular phones, smartphones, (e.g., an iPhone®), tablets (e.g., iPad®), personal digital assistants (PDAs), and the like. Wearable devices may include Fitbit Versa™ smart watch, virtual reality (VR) or augment reality (AR) systems such as magic leap 1®, HTC Vive® and Oculus®, and other devices. Gaming systems may include various handheld gaming devices, Internet-enabled gaming devices (e.g., a Microsoft Xbox® gaming console with or without a Kinect® gesture input device, Sony PlayStation® system, various gaming systems provided by Nintendo®, and others), and the like. The client devices 105 may be capable of executing various different applications such as various Internet-related apps, communication applications (e.g., E-mail applications, short message service (SMS) applications) and may use various communication protocols.

Network(s) 115 are any type of network familiar to those skilled in the art that can support data communications using any of a variety of available protocols, including without limitation TCP/IP (transmission control protocol/Internet protocol), SNA (systems network architecture), IPX (Internet packet exchange), AppleTalk®, and the like. Merely by way of example, network(s) 115 can be a local area network (LAN), networks based on Ethernet, Token-Ring, a wide-area network (WAN), the Internet, a virtual network, a virtual private network (VPN), an intranet, an extranet, a public switched telephone network (PSTN), an infra-red network, a wireless network (e.g., a network operating under any of the Institute of Electrical and Electronics (IEEE) 1002.11 suite of protocols, Bluetooth®, and/or any other wireless protocol), and/or any combination of these and/or other networks.

The network gateway 120 is a network node that forms a secure passage between two or more of the networks 115 operating in the same or different protocols. The network gateway 120 may provide network security using one or more of the following techniques: a firewall for monitoring incoming and outgoing network traffic, a virtual private network to provide private secure channels of communication, security scanning for identifying security flaws within the network(s), an access manager for authentication and authorization services, and the like. The network gateway 120 routes network traffic using a router and a service connecter that manages access to various software products, services, or systems (e.g., using a service subscription business model). The network mesh 125 is a local network topology in which the infrastructure 110 (e.g., bridges, switches, and other infrastructure devices) connect directly, dynamically and non-hierarchically to as many other nodes as possible and cooperate with one another to efficiently route data between devices and nodes. The network mesh 125 manages connections using one or more of the following techniques: load balancing, products, services, or systems discovery, network access, routing, and peering, traffic mirroring, and the like. The network(s) 115, network gateway 120, and network mesh 125 work in combination to manage all data that inflows or outflows from infrastructure 110.

The components 145 include one or more general purpose computers, specialized server computers (including, by way of example, PC (personal computer) servers, application specific servers, mid-range servers, mainframe computers, rack-mounted servers, etc.), server farms, server clusters, or any other appropriate arrangement and/or combination computers or systems that work individually or in combination to provide resources, data, services, or programs to client computing devices 105 over network(s) 115. The components 145 may further include one or more virtual machines running virtual operating systems, or other computing architectures involving virtualization such as one or more flexible pools of logical storage devices that can be virtualized to maintain virtual storage devices. In various embodiments, the components 145 are adapted to run one or more services or software applications that provide the functionality described in the present disclosure.

The components 145 also include one or more data repositories. These data repositories may be used to store data and other information in various embodiments. For example, one or more of the data repositories may be used to store information for providing data-driven technology solutions such as software as a medical device (SAMD) and store information for validation and deployment of source code to implement the data-driven technology solutions. The data repositories may reside in a variety of locations. For example, a data repository used by a component may be local to of the component or may be remote from the component and in communication with the component via a network-based or dedicated connection. Data repositories may be of different types. In certain embodiments, a data repository used by a component may be a database, for example, a centralized database, a distributed database, a NoSQL database, a relational database, or the like. One or more of these databases may be adapted to enable storage, update, and retrieval of data to and from the database in response to SQL-formatted commands. In certain embodiments, one or more of data repositories may also be used by applications to store application data. The data repositories used by applications may be of different types such as, for example, a key-value store repository, an object store repository, or a general storage repository supported by a file system.

The components 145 also include computing nodes adapted to run one or more programs such as services or software applications (e.g., the services or software applications offered as web-based or cloud services or the applications for implementing a continuous integration and continuous deployment (CI/CD) system) that provide the functionality described in the present disclosure. Each node is a representation of single machine optionally implemented within a cluster of nodes. The single machine may be a physical machine (e.g., a server in a datacenter) or a virtual machine hosted on a cloud provider such as Amazon Web Services' (AWS) with a set of a set of CPU and RAM resources that can be utilized. In clusters, the nodes pool together their resources to form a more powerful machine. When the one or more programs are deployed onto the cluster, the cluster intelligently handles distributing work to the individual nodes. If any nodes are added or removed, the cluster can shift around work as necessary. It does not matter to the one or more programs, or the infrastructure 110, which individual machines are actually running the code.

The one or more programs deployed onto one or more clusters are packaged as containers. Containers are a widely accepted standard, and various images can be defined for deploying the one or more programs on the infrastructure 110. Containerization allows for the infrastructure 110 to create self-contained execution environments. Any program and all its dependencies can be bundled up into a single file and then shared on the infrastructure 110. Creating a container can be done programmatically, allowing for powerful fully automated CI/CD pipelines to be used for validating code and deployment of code on the infrastructure 110. The containers are wrapped into a higher-level structure known as the pod 130. Containers in the same pod 130 may share the same resources and local network. In some instances, containers can communicate with other containers in the same pod 130 as though they were on the same machine while maintaining a degree of isolation from others. The pods 130 are used as the unit of replication in the infrastructure 110. If programs or resources become overwhelmed with processing and a single pod 130 instance cannot carry the load, the infrastructure 110 may be configured to deploy new replicas of a pod 130 to the cluster as necessary. Even when not under heavy load, it may be beneficial to have multiple copies of a pod 130 running at any time in a production system to allow load balancing and failure resistance. The one or more instances of the pods 130 are provisioned on the cloud infrastructure system provided by the one or more cloud service providers 140.

The cloud infrastructure system provided by the one or more cloud service providers 140 include infrastructure resources that are utilized for facilitating the provision of the one or more instances of the pods 130 supporting various cloud services offered by infrastructure 110. To facilitate efficient utilization of these resources for provisioning the one or more instances of the pods 130, the resources may be bundled into sets of resources or resource modules (also referred to as "placement rings 135" or "stateful rings 135"). Each resource module or placement ring 135 may comprise a pre-integrated and optimized combination of resources of one or more types. In certain examples, different placement rings 135 may be pre-provisioned for different types of cloud services. For example, a first set of placement rings 135 may be provisioned for a SAMD service, a second set of placement rings 135, which may include a different combination of resources than placement rings 135 in the first set of placement rings 135, may be provisioned for data analytics service, and the like. For some cloud services, the resources allocated for provisioning the services may be shared between the services.

The digital health platform 100 further includes one or more kernels 150. The kernels 150 are adapted to run on each cloud infrastructure system provided by the one or more cloud service providers 140. The kernels 150 are cluster managers that provide resource allocation and isolation across distributed applications or frameworks across the entire digital health platform 100. The kernels 150 provide the one or more programs with application programming interfaces (APIs) for orchestration of services and software including resource management and scheduling. The architecture of the kernels 150 includes agent nodes for running tasks, master nodes for sending task to the agent nodes, a zookeeper for elections and for looking up address of master nodes, and frameworks to co-ordinate with the master nodes to schedule tasks onto agent nodes.

The digital health platform 100 further includes a CI/CD system 155. The CI/CD system 155 is implemented within the cloud infrastructure system and allows the digital health platform 100 to frequently update, test, and deliver changes within source code for the software products, services, or systems. As discussed in detail herein, in healthcare, there are government regulations regarding the security of data (e.g., data integrity and data privacy) to which software must adhere. In the CI/CD system 155, these policy regulations can be included in the code, allowing compliance to be tracked, validated, and reconfigured automatically. In an example of SAMD, data storage locations, server access controls, and activity logging can be included in the source code, such that user data can be protected and managed throughout use of the software. Encryption and password-protected operations can additionally be included during continuous integration. During continuous delivery, security and monitoring tools can be used to track user activity and detect errors that could lead to a security threat.

The CI/CD system 155 may also be used for provisioning machine-learning models. Machine-learning models are initially trained using a dataset, but over time, the model may drift or the data may change, leading to a need for an updated machine-learning model. If the machine-learning model runs within a software application, code associated with the software application can include triggers for when the machine-learning model should be retrained. For example, the code may include instructions for the machine-learning model to be retrained at predefined time intervals, when new training data is available, or when the performance of the machine-learning model is determined to fall below a threshold. Additionally, software developers may explore variations in model architectures and hyperparameters in a testing environment based on monitoring the performance of the machine-learning model in a production environment or based on estimated improvements for model optimization. The CI/CD system 155 allows for easy building, testing, and deployment to a production environment when the machine-learning model is determined to meet performance requirements.

III. Security System

Figure 2:
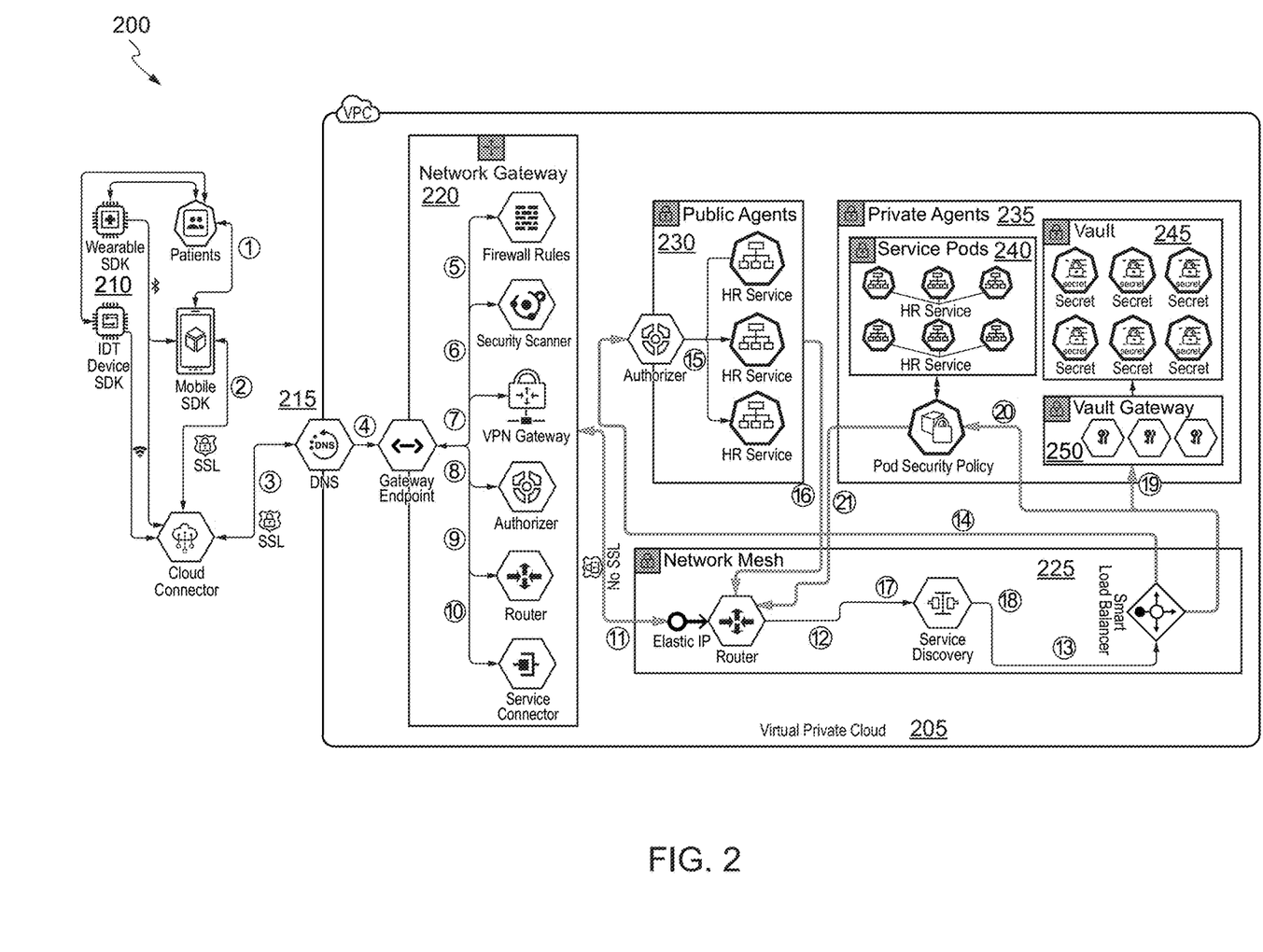
FIG. 2 depicts a diagram of a security system according to various embodiments.

FIG. 2 depicts a simplified diagram of a security system 200 (including the network gateway 120, the network mesh 125, and the pods 130 described with respect to FIG. 1) for service to service communication and authentication via a centralized network mesh in a distributed computing environment 205 in accordance with various embodiments. Although only a single distributed computing environment is shown, it should be understood that multiple distributed computing environments may be implemented within the digital health platform and each distributed computing environment would have its own set of components illustrated in FIG. 2. In the illustrated embodiment, security system 200 includes one or more client applications 210 (e.g., applications/software modules in devices that themselves are manipulated by human actors such as patients and/or service consumers), a domain name system (DNS) 215, a gateway 220, a network mesh 225, public agents 230, and private agents 235. The public agents 230 provide public services to the users 210. The private agents 235 include service pods 240, a vault 245, and a vault gateway 250, which work together to provide private services.

The client applications 210 are operated upon by users to consume the software products, services, or systems provided by the digital health platform. The client applications 210 may consume the software products, services, or systems by communication (e.g., sending requests) with the digital health platform via a distributed computing environment connector and the DNS 215. The DNS 215 is a hierarchical distributed database that stores IP addresses and other data, and allows for the IP addresses to be looked up by name for forwarding calls to the IP addresses. For example, when a request from a user is received by the digital health platform, the distributed computing environment connector identifies a distributed computing environment capable of satisfying the request, forwards the request and distributed computing environment capable of satisfying the request to the DNS 215, the DNS 215 looks up the IP addresses and other data associated with the distributed computing environment, and forwards the request to a gateway end point of the gateway (e.g., gateway 220) of the associated the distributed computing environment (e.g., distributed computing environment 205).

Once connected to the gateway end point, the client applications 210 can engage in communication with an authorizer (e.g., an access management system) to access one or more services in a session. For purposes of illustration, a "session" as described herein includes a session, or an access session, which provides a user with access to one or more services. Sessions disclosed herein may be referred to, for example, as an SSO session, an authentication session, or any other type of session that provides access to a user. Services may include, without restriction, access and functionality provided by a file, a web page, electronic content, a document, web content, a computing resource, or an application. For example, the digital health platform may include accessible services such as software products, cloud services, or systems. A service may be requested and accessed using an application. For example, an application may request access to a service from a service server based on a URL identifying a requested service. As used herein, when an action is "triggered by" or "based on" something, this means the action is triggered or based at least in part on at least a part of the something. Services may be stored and/or managed by one or more computer systems, e.g., a distributed computing system. A distributed computing system may facilitate or control access to one or more services upon authentication of a user via client applications 210.

To enable one of the services to be accessed by the client applications 210 at a client computing device, a user is requested to authenticate to establish a session (e.g., a SSO session) that provides the user via client applications 210 with access to the services. The client computing device initiates an authentication process by requesting access from the authorizer. The authentication process may include client computing device displaying one or more GUIs to receive credential information of a user and submitting a request for authentication to the authorizer. Authentication is established based on verifying user's credential information for authentication defined for the service which is requested for access. In attempting to access a service, the user operates an application (e.g., a part of the client applications 210 or a separate application) that manages access to a user's account via the authorizer. For example, the application may be an access management application that may present GUIs. Using the application and/or the client applications 210, the user requests access to one or more services, engages in authentication, and requests modification of an authentication level.

Communications between the client computing device of the user and the authorizer are received through the gateway 220. The gateway 220 supports access management services. For example, a SSO gateway may implement one or more access agents to balance and/or handle requests from client applications 210 and the authorizer. The client computing device may send/receive one or more communications to/from agents to facilitate access by the client computing device to one or more services. The authorizer may send/receive one or more communications to/from agent to facilitate access by the client computing device to one or more services. Services may be accessible to client applications 210 based on successful authentication of credential information. Upon receiving the credential information, the authorizer verifies whether a requested service, is a protected service that requires credentials for access. The authorizer determines whether access to a service is protected. Upon determining that the service is not protected, the authorizer grants access to a service (e.g., a public service). Upon determining that access to a service is protected, the authorizer determines authentication of the user via client applications 210 based on the credential information. Specifically, the authorizer collects credential information for one or more levels and/or one or more factors of authentication and the authorizer may verify whether the credential information matches credential information registered for enabling the user via client applications 210 to access the service. Upon determining authentication of user, the authorizer may determine whether the user is authorized to access a service based on access permitted to the user. The authorizer may send a communication to the client computing device to indicate an authorization of the user as to whether user is permitted to access the service. The service is then enabled as a service accessible to the user via client applications 210 upon determining that the user is authenticated and optionally authorized to access the service.

Once the service is enabled as a service accessible to the client applications 210, the gateway 220 forwards the request to the network mesh 225. The network mesh 225 is a dedicated layer built into the distributed computing environment that manages communication and networking concerns at the service level (e.g., how the various services share data with one another). Ideally, the less communications between services, the better. However, avoidance isn't always possible as services often rely on one another to complete operations. In such instances, the network mesh 225 manages and secures communications between services by (i) authenticating subsequent requests or interactions between users and various services using the authorizer, (ii) optionally encrypting communications between services, and (iii) enforcing security rules or policies (e.g., pod level security rules for communications between services within a same pod and for communications between services within different pods). In order for facilitating these operations, the network mesh 225 includes a router and one or more proxies adapted to intercept calls to and between services, and are configured with security rules or policies for controlling and routing the calls to and between services. In addition to managing and securing communications between services, the network mesh 225 may also provide support for service discovery and load balancing. For example, the network mesh 225 may retrieve a corresponding pool of service instances from a pod endpoint. The network mesh 225 then sends or routes a request to a specific service instance, recording the latency and response type of the result. The network mesh 225 may choose the instance most likely to return a fast response based on different factors, including the observed latency for recent requests.

The public agents 230 are adapted to provide one or more public services. Although these services are designated as public, this does not necessarily mean that authentication/authorization is not required for accessing the public services. In some instances, one or more level or factors of authentication and/or authorization may be required for accessing the public services. The network mesh 225 manages and secures communications between client applications 210 and public agents 230. In some instances, this includes authenticating requests or interactions between users and various public services using the authorizer and routing calls to and between services provided by the public agents 230 while enforcing security rules or policies.

The private agents 235 are adapted to provide one or more private services contained within service pods 240 (e.g., a first service with a first pod and a second service within a second pod). The network mesh 225 manages and secures communications between client applications 210 and private agents 235. In some instances, this includes routing calls to and between services provided by the private agents 235 while enforcing security rules or policies. The private agents 235 utilize a vault 245 and vault gateway 250 for managing and storing security keys or access keys used by each service to communicate with and access other services. The vault gateway 250 is a network node that forms a secure passage between the services and the vault 245. The vault gateway 250 may provide vault network security using one or more of the following techniques: a firewall for monitoring incoming and outgoing network traffic, a virtual private network to provide private secure channels of communication, security scanning for identifying security flaws within the network(s), an access manager for authentication and authorization services, and the like. The vault gateway 250 routes vault traffic using a router and a service connecter that manages access to the vault and various secrets, i.e., the security or access keys.

The vault 245 manages and stores the security keys or access keys. The security keys are short-term credentials for a service to communicate with and gain access to another services. The security keys may be used to sign programmatic requests to the another services (e.g., the application programming interface of the another service.). A security key is comprised of an access identifier and a secret access key. Like a user name and password, the service must use both the access identifier and a secret access key together to authenticate access requests. The security keys may be managed using one or more rules or policies stored in a data store ("policies") to control access to services. The policies define the other services that can be accessed by each service. For example, an administrator may only allow certain services to be accessed by a particular service in order to maintain isolation between services and/or data privacy. The vault 245 determines which services get which security keys for accessing other services based on the one or more of policies.

IV. Techniques for Deployment of a Service on a Digital Health Platform

Figure 3:
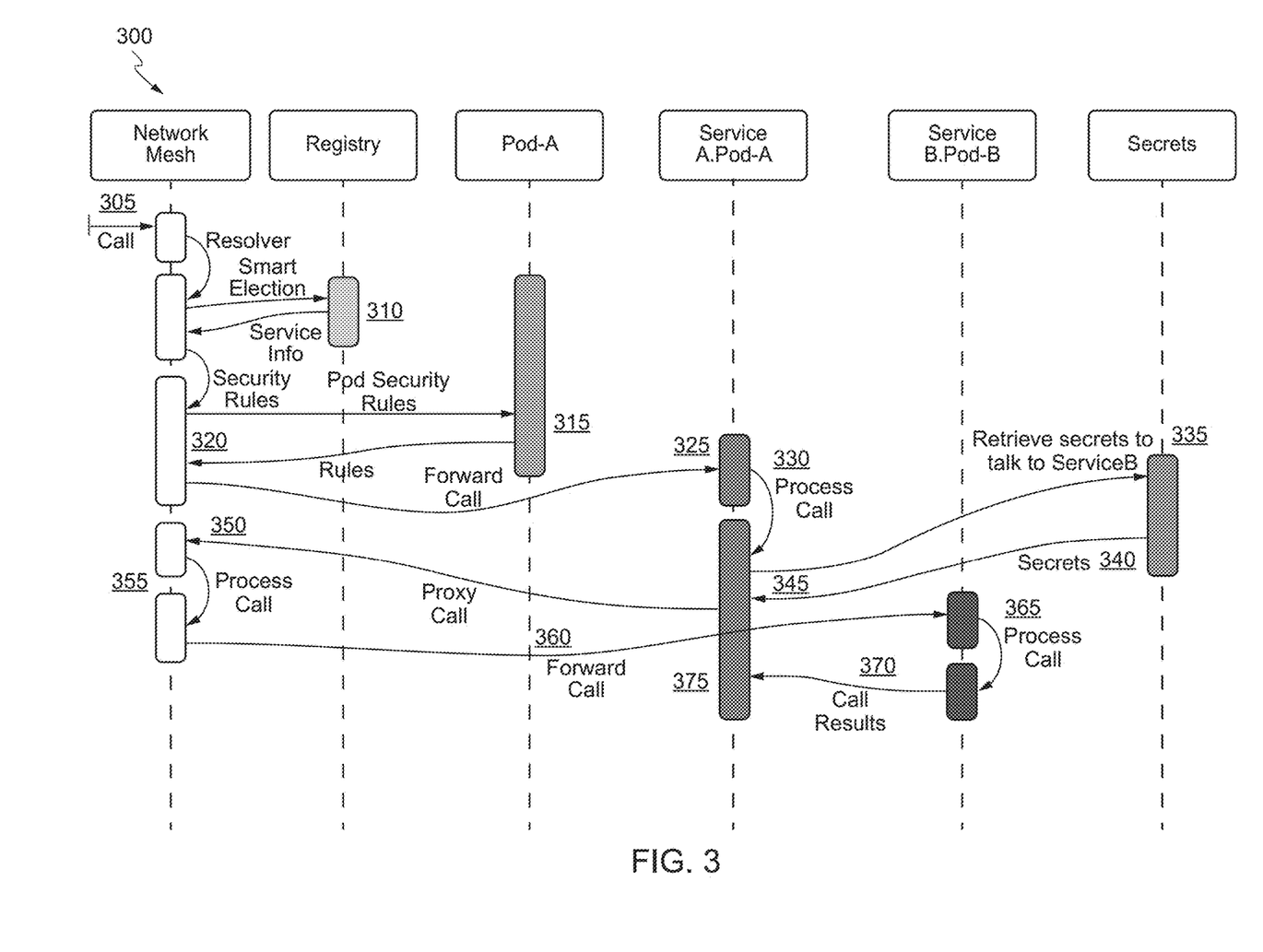
FIG. 3 depicts a swim lane diagram illustrating a process for service to service communication and authentication in a digital health platform according to various embodiments.
Figure 4:
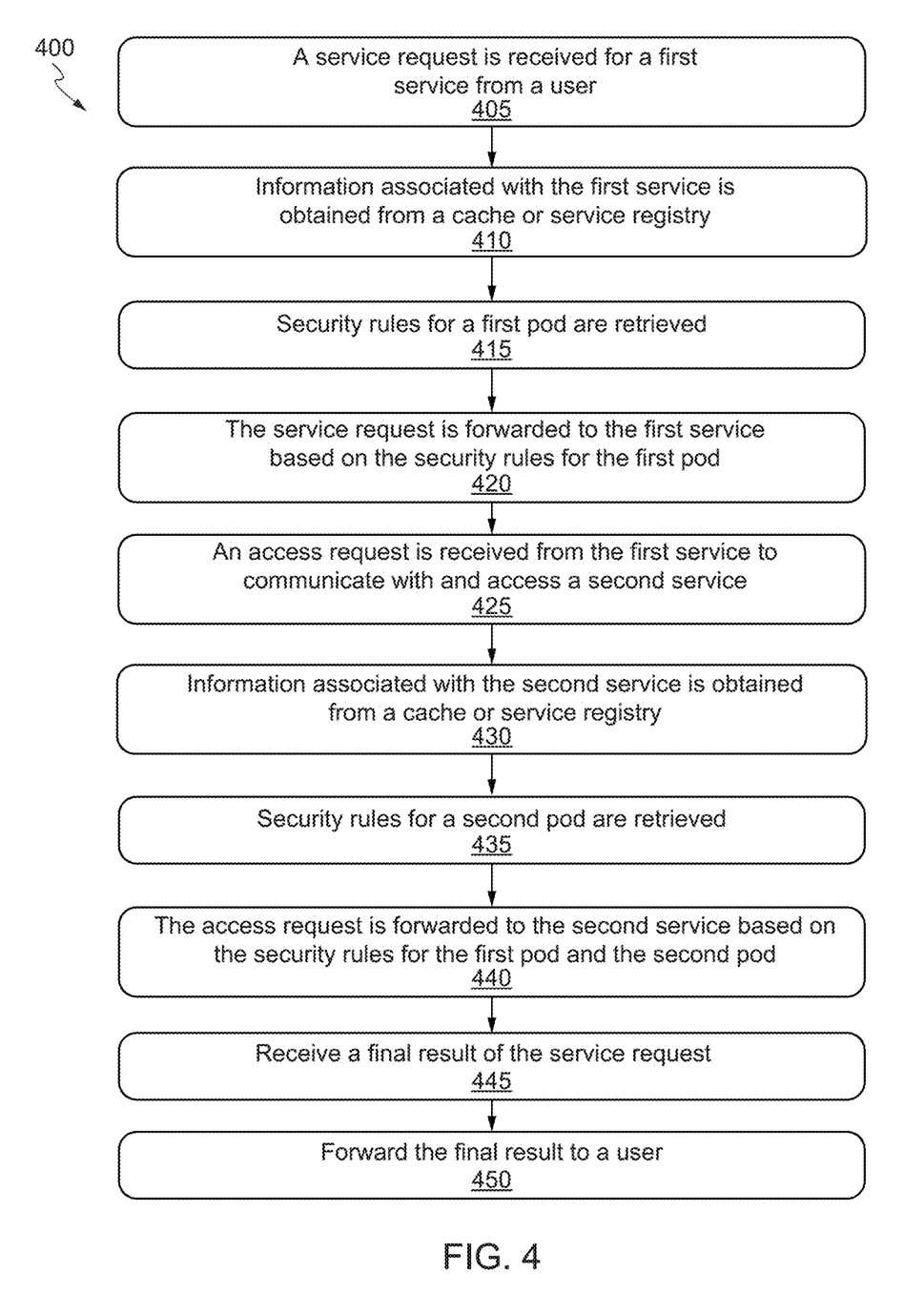
FIG. 4 depicts a flowchart illustrating a process for service to service communication and authentication via a centralized network mesh environment according to various embodiments.

FIGS. 3 and 4 illustrate processes and operations for service to service communication and authentication via a centralized network mesh. Individual embodiments may be described as a process which is depicted as a flowchart, a flow diagram, a data flow diagram, a structure diagram, or a block diagram. Although a flowchart may describe the operations as a sequential process, many of the operations may be performed in parallel or concurrently. In addition, the order of the operations may be re-arranged. A process is terminated when its operations are completed, but could have additional steps not included in a figure. A process may correspond to a method, a function, a procedure, a subroutine, a subprogram, etc. When a process corresponds to a function, its termination may correspond to a return of the function to the calling function or the main function.

The processes and/or operations depicted in FIGS. 3 and 4 may be implemented in software (e.g., code, instructions, program) executed by one or more processing units (e.g., processors cores), hardware, or combinations thereof. The software may be stored in a memory (e.g., on a memory device, on a non-transitory computer-readable storage medium). The particular series of processing steps in FIGS. 3 and 4 is not intended to be limiting. Other sequences of steps may also be performed according to alternative embodiments. For example, in alternative embodiments the steps outlined above may be performed in a different order. Moreover, the individual steps illustrated in FIGS. 3 and 4 may include multiple sub-steps that may be performed in various sequences as appropriate to the individual step. Furthermore, additional steps may be added or removed depending on the particular applications. One of ordinary skill in the art would recognize many variations, modifications, and alternatives.

FIG. 3 illustrates a process 300 for service to service communication and authentication in a digital health platform. The processes depicted in flowchart 300 are implemented by the architecture, systems, and techniques depicted in FIGS. 1 and 2.

At step 305, the network mesh receives a service request (e.g., a request for access to a service such as a service A from a user). The network mesh resolves the request by determining whether the network mesh is familiar with the service. This determination may be made by determining whether the network mesh has any data on the service in a cache. The cache is a hardware or software component that stores data (e.g. information on various services) so that future requests for that data can be served faster. The data stored in a cache may be the result of an earlier request for a service or a copy of data stored elsewhere. When the network mesh has data on the service in the cache, the network mesh obtains the data from the cache. The data includes identification of one or more pods (e.g., pod A) comprising the service (e.g., service A) and a location of the one or more pods within a distributed computing environment. The location may include the specific distributed computing environment, nodes, cluster of nodes, instance of the nodes or cluster, or a combination thereof running the one or more pods. The data informs the network mesh of which pods are encapsulating the service (e.g., govern the service) and how to contact the pods encapsulating the service (e.g., IP addresses of pods within a distributed computing environment).

At step 310, when the network mesh does not have data on the service in the cache, the network mesh contacts a data registry to obtain the data on the service. The data registry is a single point of truth storing data regarding all services running on the digital health platform (e.g., multiple distributed computing environments). As with the cache, the data informs the network mesh of which pods are encapsulating the service (e.g., govern the service) and how to contact the pods encapsulating the service (e.g., IP addresses of pods within a distributed computing environment). The data retrieved by the network mesh from the registry may be stored within the cache for downstream processing and future requests.

At step 315, the network mesh communicates with the one or more pods (e.g., pod A) encapsulating the service based on the data obtained from the cache or registry. The communication includes a request from the network mesh for security rules for the one or more pods. The security rules define: (i) a unique address identifier for the service, and (ii) services that the service is authorized to communicate with and access. For example, the security rules for pod A define a unique address identifier for service A and services that service A is authorized to communicate with and access. When each pod is created, each pod is assigned rules or policies that govern other pods or services that may be communicated with and accessed by services encapsulated by each pod. The rule or policies may be written by an administrator such as an administrator of the digital health platform. Moreover, when created, each service is assigned a unique address identifier address. This address is tied to the lifespan of the service, and will not change while the service is active. The network mesh and pods communicate with the service via the unique address identifier, and that communication to the service may be governed by the rules or policies and automatically load-balanced out to an instance of the pod that encapsulates the service.

At step 320, the security rules for the one or more pods are retrieved from the one or more pods (e.g., pod A). The one or more pods receive the request from the network mesh for security rules, obtain the security rules from a data storage device, and forward the security rules to the network mesh.

At step 325, the service request is forwarded to the service (e.g., service A) based on the security rules. For example, the network mesh uses the unique address identifier for the service to communicate with and forward the resource request to the resource. In some instances, the network mesh uses the unique address identifier and a proxy associated with service to communicate with and forward the service request to the service. The proxy may then be used for any subsequent communication with the service regarding the service request.

At step 330, the service receives and processes the service request. The processing includes the service executing one or more program operations in order to satisfy the service request. For example, for a service request, the service may execute one or more operations for providing the service such as collection of medical data, transformation of medical data, communication of medical data, and the like. In some instances, as a part of satisfying the service request, the service may need to communicate with and access other services (e.g., retrieve data from a separate data storage device such as service B) on other pods (e.g., pod B). In such instances, at step 335, the service connects with a vault to obtain a secret key for communicating with and accessing another service on another pod.

At step 335, the vault connects with the service and uses one or more rules or policies stored in a data store to control access to the another service. For example, upon connection with the service, the vault determines whether the service is authorized to communicate with and access the another service based on the one or more of policies. When the service is authorized to communicate with and access the another service based on the one or more of policies, the vault retrieves a security key for the another service, and at step 340 forwards the security key to the service. When the service is not authorized to communicate with and access the another service based on the one or more of policies, the vault notifies the services that it is not authorized to communicate with and access the another service.

At step 345, when the service is authorized to communicate with and access the another service, the service receives the security key for the another service and embeds the security key in an access request to the another service. For example, the service may generate an access request that requests the another service to perform one or more program operations in order to assist in satisfying the service request. The access request may be signed using the security key.

At step 350, the service communicates the access request with the network mesh. In some instances, the service communicates the access request with the network mesh via the proxy associated with service. The service communicates the access request to the network mesh because (i) the service does not have a unique address identifier for the service, and (ii) to allow the network mesh to maintain control and security over all service to service communications.

At step 355, the network mesh receives and processes the access request from the service. The processing the access request is similar to the processing of the service request described with respect to steps 305-325 (not shown in FIG. 3).

At step 360, the network mesh forwards the access request from the service to the another service based on the security rules for the pod (e.g., pod A) associated with the service and the security rules for the pod (e.g., pod B) associated with the another service. In some instances, the network mesh forwards the access request from the service to the another service via the proxy associated with service. The forwarding comprises the network mesh determining whether the security rules for the pod (e.g., pod A) define the another service (e.g., service B) as a service that the service (e.g., service A) is authorized to communicate with and access, and determining whether the security rules for the another pod (e.g., pod B) define the service (e.g., service A) as a service that the another service (e.g., service B) is authorized to receive communication from and allow to access. When the another service (e.g., service B) is a service that the service (e.g., service A) is authorized to communicate with and access and the service (e.g., service A) is a service that the another service (e.g., service B) is authorized to receive communication from and allow to access, forwarding the access request from the service to the another service.

At step 365, the another service receives the access request from the network mesh and validates the security key. When the security key is invalid, the another service directly notifies the service of the invalid security key. When the security key is valid, the another service processes the access request. The processing includes the another service executing the one or more program operations in order assist in satisfying the service request. For example, for a service request, the service may execute one or more operations for providing the service such as collection of medical data, transformation of medical data, communication of medical data, and the like.

At step 370, the another service communicates a result of processing the access request directly back to the service. In some instances, the another service communicates results of the access request with the service via the proxy associated with service.

At step 375, the service receives the results of the access request, and integrates the result of the access request with results of the service processing the service request to generate a final result for the service request. The service may then output the final results of the service request to the networking mesh, which in turn communicates the final results of the service request, for example, to the user via the network gateway.

FIG. 4 illustrates a process 400 for service to service communication and authentication via a centralized network mesh. At step 405, a network mesh receives a service request for a first service, for example, from a user. In some instances, the service request is a request for a service and the first service is a first service. The first service may comprises one or more programs deployed onto one or more clusters packaged as a first container or first set of containers on a first distributed computing environment, and the first container or the first set of containers may be packaged as a first pod, which is a higher-level structure that represents the one or more programs running on the one or more clusters.

At step 410, the network mesh obtains information associated with the first service from a cache or service registry. The information includes identification of the first pod comprising the first service and a location of the first pod within the first distributed computing environment. The obtaining the information may comprises: (i) determining whether the information associated with the first service is available from the cache; (ii) when the information associated with the first service is available from the cache, obtaining the information associated with the first service from the cache; (iii) when the information associated with the first service is not available from the cache, obtaining the information associated with the first service from the registry; and (iv) in response to obtaining the information associated with the first service from the registry, storing the information associated with the first service in the cache for subsequent requests.

At step 415, the network mesh, using the location of the first pod, retrieves security rules for the first pod. The security rules define: (i) a unique address identifier for the first service, and (ii) services that the first service is authorized to communicate with and access. In some instances, the security rules further define: (iii) a number of instances available for the first service, and (iv) which instances are available for processing the service request.

At step 420, the network mesh forwards the service request to the first service based on the security rules for the first pod. The forwarding comprises: (i) determining the instances that are available for processing the service request based on the security rules for the first pod, and (ii) forwarding the service request to at least one of the instances of the first service using the unique address identifier for the first service.

At step 425, the network mesh receives an access request from the first service to communicate with and access a second service. The second service may comprise one or more programs deployed onto one or more clusters packaged as a second container or second set of containers on the first distributed computing environment or a second distributed computing environment, and the second container or the second set of containers may be packaged as a second pod, which is a higher-level structure that represents the one or more programs running on the one or more clusters. The access request includes a security key specific to the second service. The security key is obtained by the first service from a vault, and the first service embeds the security key into the access request. The access request may also include a request of the second service to perform one or more operations and/or acquire services on behalf of the first service. In some instances, the access request is a request for a service and the second service is a second service.

At step 430, the network mesh obtains information associated with the second service from the cache or the service registry. The information includes identification of the second pod comprising the second service and a location of the second pod within the first distributed computing environment or the second distributed computing environment. In some instances, the second pod is located within the second distributed computing environment, which is different from the first distributed computing environment. The obtaining the information may comprises: (i) determining whether the information associated with the second service is available from the cache; (ii) when the information associated with the second service is available from the cache, obtaining the information associated with the second service from the cache; (iii) when the information associated with the second service is not available from the cache, obtaining the information associated with the second service from the registry; and (iv) in response to obtaining the information associated with the second service from the registry, storing the information associated with the second service in the cache for subsequent requests.

At step 435, the network mesh, using the location of the second pod, retrieves security rules for the second pod. The security rules define: (i) a unique address identifier for the second service, and (ii) services that the second service is authorized to communicate with and access. In some instances, the security rules further define: (iii) a number of instances available for the second service, and (iv) which instances are available for processing the access request.

At step 440, the network mesh forwards the access request to the second service based on the security rules for the first pod and the security rules for the second pod. The forwarding comprises: (i) determining whether the security rules for the second pod define the second service as a service that the first service is authorized to communicate with and access; (ii) determining whether the security rules for the second pod define the first service as a service that the second service is authorized to receive communication from and allow to access; (iii) and when the second service is a service that the first service is authorized to communicate with and access and the first service is a service that the second service is authorized to receive communication from and allow to access, forwarding the access request from the first service to the second service using the unique address identifier for the second service. In some instances, the forwarding further comprises: (iv) determining the instances that are available for processing the access request based on the security rules for the second pod, and forwarding the access request to at least one of the instances of the second service using the unique address identifier for the second service. The second service may perform the one or more operations and/or acquire the services on behalf of the first service, and may generate a sub result based on the performance of the one or more operations and/or acquisition of the services. The second service may validate the security key prior to performing the one or more operations and/or acquiring the services on behalf of the first service.

At step 445, the network mesh receives a final result of the service request from the first service. The final result includes the sub result obtained from the second service.

At step 450, the network mesh outputs the final result of the service request, and in some instances communicates the final results, for example to the user.

V. Additional Considerations

Some embodiments of the present disclosure include a system including one or more data processors. In some embodiments, the system includes a non-transitory computer readable storage medium containing instructions which, when executed on the one or more data processors, cause the one or more data processors to perform part or all of one or more methods and/or part or all of one or more processes disclosed herein. Some embodiments of the present disclosure include a computer-program product tangibly embodied in a non-transitory machine-readable storage medium, including instructions configured to cause one or more data processors to perform part or all of one or more methods and/or part or all of one or more processes disclosed herein.

The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention as claimed has been specifically disclosed by embodiments and optional features, modification and variation of the concepts herein disclosed may be resorted to by those skilled in the art, and that such modifications and variations are considered to be within the scope of this invention as defined by the appended claims.

The ensuing description provides preferred exemplary embodiments only, and is not intended to limit the scope, applicability or configuration of the disclosure. Rather, the ensuing description of the preferred exemplary embodiments will provide those skilled in the art with an enabling description for implementing various embodiments. It is understood that various changes may be made in the function and arrangement of elements without departing from the spirit and scope as set forth in the appended claims.

Specific details are given in the following description to provide a thorough understanding of the embodiments. However, it will be understood that the embodiments may be practiced without these specific details. For example, circuits, systems, networks, processes, and other components may be shown as components in block diagram form in order not to obscure the embodiments in unnecessary detail. In other instances, well-known circuits, processes, algorithms, structures, and techniques may be shown without unnecessary detail in order to avoid obscuring the embodiments.

What is claimed is:

1. A computer-implemented method comprising:
   receiving, at a network mesh, a service request for a first service;
   obtaining, by the network mesh, information associated with the first service from a cache or service registry, wherein the information includes identification of a first pod comprising the first service and a location of the first pod within a first distributed computing environment;
   retrieving, by the network mesh using the location of the first pod, security rules for the first pod, wherein the security rules define: (i) a unique address identifier for the first service, and (ii) services that the first service is authorized to communicate with and access;
   forwarding, by the network mesh using the unique address identifier for the first service, the service request to the first service;
   receiving, by the network mesh, an access request from the first service to communicate with and access a second service, wherein the access request includes a security key specific to the second service;
   obtaining, by the network mesh, information associated with the second service from the cache or the service registry, wherein the information includes identification of a second pod comprising the second service and a location of the second pod within the first distributed computing environment or a second distributed computing environment; and
   retrieving, by the network mesh using the location of the second pod, security rules for the second pod, wherein the security rules define (i) a unique address identifier for the second service, and (ii) services that the second service is authorized to communicate with and access;
   forwarding, by the network mesh using the unique address identifier for the second service, the access request from the first service to the second service based on the security rules for the first pod and the security rules for the second pod;
   receiving, by the network mesh, a final result of the service request from the first service, wherein the final result includes a sub result obtained from the second service; and
   outputting, by the network mesh, the final result of the service request.

2. The computer-implemented method of claim 1, wherein the obtaining the information associated with the first service or the second service comprises:
   determining whether the information associated with the first service or the second service is available from the cache;
   when the information associated with the first service or the second service is available from the cache, obtaining the information associated with the first service or the second service from the cache;
   when the information associated with the first service or the second service is not available from the cache, obtaining the information associated with the first service or the second service from the registry; and
   in response to obtaining the information associated with the first service or the second service from the registry, storing the information associated with the first service or the second service in the cache for subsequent requests.

3. The computer-implemented method of claim 1, wherein the security key is obtained by the first service from a vault, and the first service embeds the security key into the access request.

4. The computer-implemented method of claim 3, wherein the access request from the first service further includes a request of the second service to perform one or more operations and/or acquire services on behalf of the first service.

5. The computer-implemented method of claim 4, wherein the second service performs the one or more operations and/or acquires the services on behalf of the first service; and generates the sub result based on the performance of the one or more operations and/or acquisition of the services.

6. The computer-implemented method of claim 5, wherein the second service validates the security key prior to performing the one or more operations and/or acquiring the services on behalf of the first service.

7. The computer-implemented method of claim 1, wherein the second pod is located within the second distributed computing environment, which is different from the first distributed computing environment.

8. The computer-implemented method of claim 1, wherein the security rules for the first pod further define: (i) a number of instances available for the first service, and (ii) which instances are available for processing the service request, and wherein the forwarding the service request to the first service comprises:
determining the instances that are available for processing the service request based on the security rules for the first pod; and
forwarding the service request to at least one of the instances of the first service.

9. The computer-implemented method of claim 1, wherein the forwarding the access request from the first service to the second service comprises:
determining whether the security rules for the first pod define the second service as a service that the first service is authorized to communicate with and access;
determining whether the security rules for the second pod define the first service as a service that the second service is authorized to receive communication from and allow to access;
and when the second service is a service that the first service is authorized to communicate with and access and the first service is a service that the second service is authorized to receive communication from and allow to access, forwarding the access request from the first service to the second service.

10. The computer-implemented method of claim 9, wherein the security rules for the second pod further define: (i) a number of instances available for the second service, and (ii) which instances are available for processing the access request, and wherein the forwarding the access request from the first service to the second service further comprises:
determining the instances that are available for processing the access request based on the security rules for the second pod; and
forwarding the access request to at least one of the instances of the second service.

11. The computer-implemented method of claim 1, wherein:
the first service comprises one or more programs deployed onto one or more clusters packaged as a first container or first set of containers on the first distributed computing environment, and the first container or the first set of containers are packaged as the first pod, which is a higher-level structure that represents the one or more programs running on the one or more clusters; and
the second service comprises one or more programs deployed onto one or more clusters packaged as a second container or second set of containers on the first distributed computing environment or a second distributed computing environment, and the second container or the second set of containers are packaged as the second pod, which is a higher-level structure that represents the one or more programs running on the one or more clusters.

12. A system comprising:
one or more data processors of a network mesh; and
a non-transitory computer readable storage medium containing instructions which, when executed on the one or more data processors, cause the one or more data processors to perform actions including:
receiving a service request for a first service;
obtaining information associated with the first service from a cache or service registry, wherein the information includes identification of a first pod comprising the first service and a location of the first pod within a first distributed computing environment;
retrieving, using the location of the first pod, security rules for the first pod, wherein the security rules define: (i) a unique address identifier for the first service, and (ii) services that the first service is authorized to communicate with and access;
forwarding, using the unique address identifier for the first service, the service request to the first service;
receiving an access request from the first service to communicate with and access a second service, wherein the access request includes a security key specific to the second service;
obtaining information associated with the second service from the cache or the service registry, wherein the information includes identification of a second pod comprising the second service and a location of the second pod within the first distributed computing environment or a second distributed computing environment; and
retrieving, using the location of the second pod, security rules for the second pod, wherein the security rules define (i) a unique address identifier for the second service, and (ii) services that the second service is authorized to communicate with and access;
forwarding, using the unique address identifier for the second service, the access request from the first service to the second service based on the security rules for the first pod and the security rules for the second pod;
receiving a final result of the service request from the first service, wherein the final result includes a sub result obtained from the second service; and
outputting the final result of the service request.

13. The system of claim 12, wherein the obtaining the information associated with the first service or the second service comprises:
determining whether the information associated with the first service or the second service is available from the cache;
when the information associated with the first service or the second service is available from the cache, obtaining the information associated with the first service or the second service from the cache;
when the information associated with the first service or the second service is not available from the cache, obtaining the information associated with the first service or the second service from the registry; and
in response to obtaining the information associated with the first service or the second service from the registry, storing the information associated with the first service or the second service in the cache for subsequent requests.

14. The system of claim 12, wherein the security key is obtained by the first service from a vault, and the first service embeds the security key into the access request, and wherein the access request from the first service further includes a request of the second service to perform one or more operations and/or acquire services on behalf of the first service.

15. The system of claim 14, wherein the second service performs the one or more operations and/or acquires the services on behalf of the first service; and generates the sub result based on the performance of the one or more operations and/or acquisition of the services, and wherein the second service validates the security key prior to performing the one or more operations and/or acquiring the services on behalf of the first service.

16. The system of claim 12, wherein the second pod is located within the second distributed computing environment, which is different from the first distributed computing environment.

17. The system of claim 12, wherein the security rules for the first pod further define: (i) a number of instances available for the first service, and (ii) which instances are available for processing the service request, and wherein the forwarding the service request to the first service comprises:
  determining the instances that are available for processing the service request based on the security rules for the first pod; and
  forwarding the service request to at least one of the instances of the first service.

18. The system of claim 12, wherein the forwarding the access request from the first service to the second service comprises:
  determining whether the security rules for the first pod define the second service as a service that the first service is authorized to communicate with and access;
  determining whether the security rules for the second pod define the first service as a service that the second service is authorized to receive communication from and allow to access;
  and when the second service is a service that the first service is authorized to communicate with and access and the first service is a service that the second service is authorized to receive communication from and allow to access, forwarding the access request from the first service to the second service.

19. The system of claim 18, wherein the security rules for the second pod further define: (i) a number of instances available for the second service, and (ii) which instances are available for processing the access request, and wherein the forwarding the access request from the first service to the second service further comprises:
  determining the instances that are available for processing the access request based on the security rules for the second pod; and
  forwarding the access request to at least one of the instances of the second service.

20. A computer-program product tangibly embodied in a non-transitory machine-readable storage medium, including instructions configured to cause one or more data processors of a network mesh to perform actions including:
  receiving a service request for a first service;
  obtaining information associated with the first service from a cache or service registry, wherein the information includes identification of a first pod comprising the first service and a location of the first pod within a first distributed computing environment;
  retrieving, using the location of the first pod, security rules for the first pod, wherein the security rules define: (i) a unique address identifier for the first service, and (ii) services that the first service is authorized to communicate with and access;
  forwarding, using the unique address identifier for the first service, the service request to the first service;
  receiving an access request from the first service to communicate with and access a second service, wherein the access request includes a security key specific to the second service;
  obtaining information associated with the second service from the cache or the service registry, wherein the information includes identification of a second pod comprising the second service and a location of the second pod within the first distributed computing environment or a second distributed computing environment; and
  retrieving, using the location of the second pod, security rules for the second pod, wherein the security rules define (i) a unique address identifier for the second service, and (ii) services that the second service is authorized to communicate with and access;
  forwarding, using the unique address identifier for the second service, the access request from the first service to the second service based on the security rules for the first pod and the security rules for the second pod;
  receiving a final result of the service request from the first service, wherein the final result includes a sub result obtained from the second service; and
  outputting the final result of the service request.

* * * * *